US007992228B2

(12) United States Patent
Milea et al.

(10) Patent No.: US 7,992,228 B2
(45) Date of Patent: Aug. 9, 2011

(54) PROTECTIVE EYEWEAR

(75) Inventors: Eduard U. Milea, Allston, MA (US); Kyle L. Lamson, Chelmsford, MA (US)

(73) Assignee: Warrior Sports, Inc., Warren, MI (US)

( * ) Notice: Subject to any disclaimer, the term of this patent is extended or adjusted under 35 U.S.C. 154(b) by 337 days.

(21) Appl. No.: 12/416,482

(22) Filed: Apr. 1, 2009

(65) Prior Publication Data
US 2010/0251465 A1    Oct. 7, 2010

(51) Int. Cl.
*A61F 9/02* (2006.01)
(52) U.S. Cl. ............................. 2/448; 2/452; 2/426
(58) Field of Classification Search .............. 2/252, 445, 2/426, 431, 452, 9, 448, 439, 428; 351/156, 351/157
See application file for complete search history.

(56) References Cited

U.S. PATENT DOCUMENTS

| | | | | |
|---|---|---|---|---|
| 2,504,524 | A * | 4/1950 | Hayward | 2/445 |
| 2,758,308 | A * | 8/1956 | Ellis | 2/452 |
| 3,457,564 | A * | 7/1969 | Holloway | 2/8.1 |
| 4,077,068 | A * | 3/1978 | Anderson | 2/428 |
| 4,264,987 | A * | 5/1981 | Runckel | 2/428 |
| 4,527,291 | A | 7/1985 | Nussbickl | |
| 4,991,952 | A | 2/1991 | Grau | |
| 5,303,428 | A * | 4/1994 | Pernicka | 2/452 |
| 5,313,665 | A | 5/1994 | Luczenbacher, Sr. et al. | |
| 5,406,340 | A * | 4/1995 | Hoff | 351/156 |
| 5,408,702 | A * | 4/1995 | Chiang | 2/428 |
| 5,410,763 | A * | 5/1995 | Bolle | 2/436 |
| 5,652,954 | A * | 8/1997 | Paiement et al. | 2/10 |
| 5,706,526 | A * | 1/1998 | Huang | 2/428 |
| 5,727,259 | A * | 3/1998 | Kawamata | 2/452 |
| 5,799,338 | A * | 9/1998 | Huang | 2/428 |
| 5,802,622 | A * | 9/1998 | Baharad et al. | 2/434 |
| 6,321,391 | B1 * | 11/2001 | Basso | 2/452 |
| 6,349,420 | B1 * | 2/2002 | Chiang | 2/428 |
| 6,449,777 | B1 * | 9/2002 | Montague | 2/452 |
| 6,477,717 | B1 * | 11/2002 | Winefordner et al. | 2/428 |
| 6,574,802 | B2 * | 6/2003 | Chiang | 2/428 |
| 6,715,157 | B2 * | 4/2004 | Mage | 2/439 |
| 6,817,068 | B2 * | 11/2004 | Cleary et al. | 24/3.13 |
| 7,003,811 | B2 | 2/2006 | Canavan | |
| 7,162,750 | B2 * | 1/2007 | Canavan | 2/448 |
| 7,322,692 | B2 | 1/2008 | Winningham | |
| 2005/0051164 | A1 | 3/2005 | Hutter et al. | |

OTHER PUBLICATIONS

Great Atlantic Lacrosse Company Catalog, p. 63, Dec. 2008.

* cited by examiner

*Primary Examiner* — Danny Worrell
(74) *Attorney, Agent, or Firm* — Warner Norcross & Judd LLP

(57) ABSTRACT

Protective eyewear includes a frame having a first and second opposing sides and an eye protector joined with the frame. A flexible strap is joined with the first and second sides of the frame. The strap extends around at least a portion of a player's head to position the eye protector over the player's eyes. A connector is rotatably joined with the first side of the frame so that the connector rotates in a plane generally parallel to a temple of the player. The connector is joined with the strap so that the strap can rotate relative to the frame and includes a limiter that limits the rotation of the connector. A strap diverter is adjustably positioned along the strap and divides the strap into first and second strap portions that extend at an angle relative to one another and define a space therebetween.

20 Claims, 5 Drawing Sheets

PROTECTIVE EYEWEAR

BACKGROUND OF THE INVENTION

The present invention relates generally to protective sports equipment, and more particularly to protective eyewear for use during sports such as lacrosse and field hockey.

Lacrosse and field hockey are rough contact sports, and injuries to players are not uncommon. Such injuries can be caused by bodily contact with another player or by being struck with a stick. Contact with a lacrosse ball can also cause injuries because lacrosse balls are relatively heavy and travel at high speeds during play. As a result, players use a variety of protective equipment to avoid these injuries. For example, players typically use protective gloves, arm pads, shoulder pads, helmets and face guards.

Some types protective equipment have been adapted specifically for male and female players. For example, male players often use helmets with metal wire cage face guards, while female players typically use a smaller protective eyewear device, such as goggles. Goggles, however, typically include a polycarbonate lens and can produce glare in the sun. They can also fog up, particularly in cold, wet or humid weather. Further, goggles can impede a player's vision and can be easily scratched or shattered.

Conventional goggles typically include an elastic strap that travels around the player's head to secure the goggles over the player's eyes. Such a strap is impractical for female players, who typically tie their hair back, for example, in a ponytail. A female player can adjust the strap to travel above her ponytail, but the strap will likely pull the goggles upward on her face. Additionally, positioning the strap too high on the player's head can allow the elastic force of the strap to slide the strap over the player's head, which may cause the goggles to fall off. Alternatively, the player can adjust the strap below her ponytail, which can pull the goggles downward on the player's face and ears.

SUMMARY OF THE INVENTION

The present invention provides a protective eyewear device that is comfortable for players and that reliably maintains its position on a player's face and head.

In one embodiment, the protective eyewear includes a frame having a first side and an opposing second side. An eye protector is joined with the frame. A flexible strap is joined with the first and second sides of the frame. The strap extends around at least a portion of a player's head to position the eye protector over the player's eyes. A connector is rotatably joined with the first side of the frame, so that the connector rotates in a plane generally parallel to a temple of the player, and is joined with the strap so that the strap can rotate relative to the frame. The connector can include a rotation limiter that limits the rotation of the connector.

In another embodiment, a strap diverter is adjustably positioned along the strap and divides the strap into first and second strap portions that extend at an angle relative to one another and define a space therebetween. Optionally, the eyewear includes first and second strap diverters positioned along the strap. The first diverter can divert the first and second strap portions in different directions to create a space between the first and second strap portions. The second diverter can converge the first and second strap portions so that they are overlapped as they exit the second diverter. The positions of the first and second diverters may be adjustable along the strap.

In yet another embodiment, the connector can include a base and a swivel portion joined together. The swivel portion can be at least partially rotatably mounted in an aperture defined in the frame, and the base can be non-rotatable relative to the frame. Optionally, the rotation limiter can be formed as an abutment portion that is positioned on the base and adapted to engage the swivel portion to limit its rotational movement.

The protective eyewear device of the present invention can provide a variety of features that comfortably maintain the position of the device on a player's face and head. The connectors that join the frame and strap maintain the adjustability of the strap, while preventing the strap from rotating so far up on the player's head that the strap causes the strap to slide off the player's head. Where used, the strap diverters separate the strap into sections to evenly distribute the elastic force of the strap on the player's head, such that the frame is pulled generally directly against the player's face, rather than up or down on the face. Further, where used, the strap diverters can be adjusted to vary the size of the space between the two strap sections, which can allow the player to not only vary the distribution of the force of the strap on the head, but also vary the placement of the player's ponytail, if the player is female.

These and other objects, advantages, and features of the invention will be more fully understood and appreciated by reference to the description of the current embodiment and the drawings.

DESCRIPTION OF THE CURRENT EMBODIMENT

Figure 1:
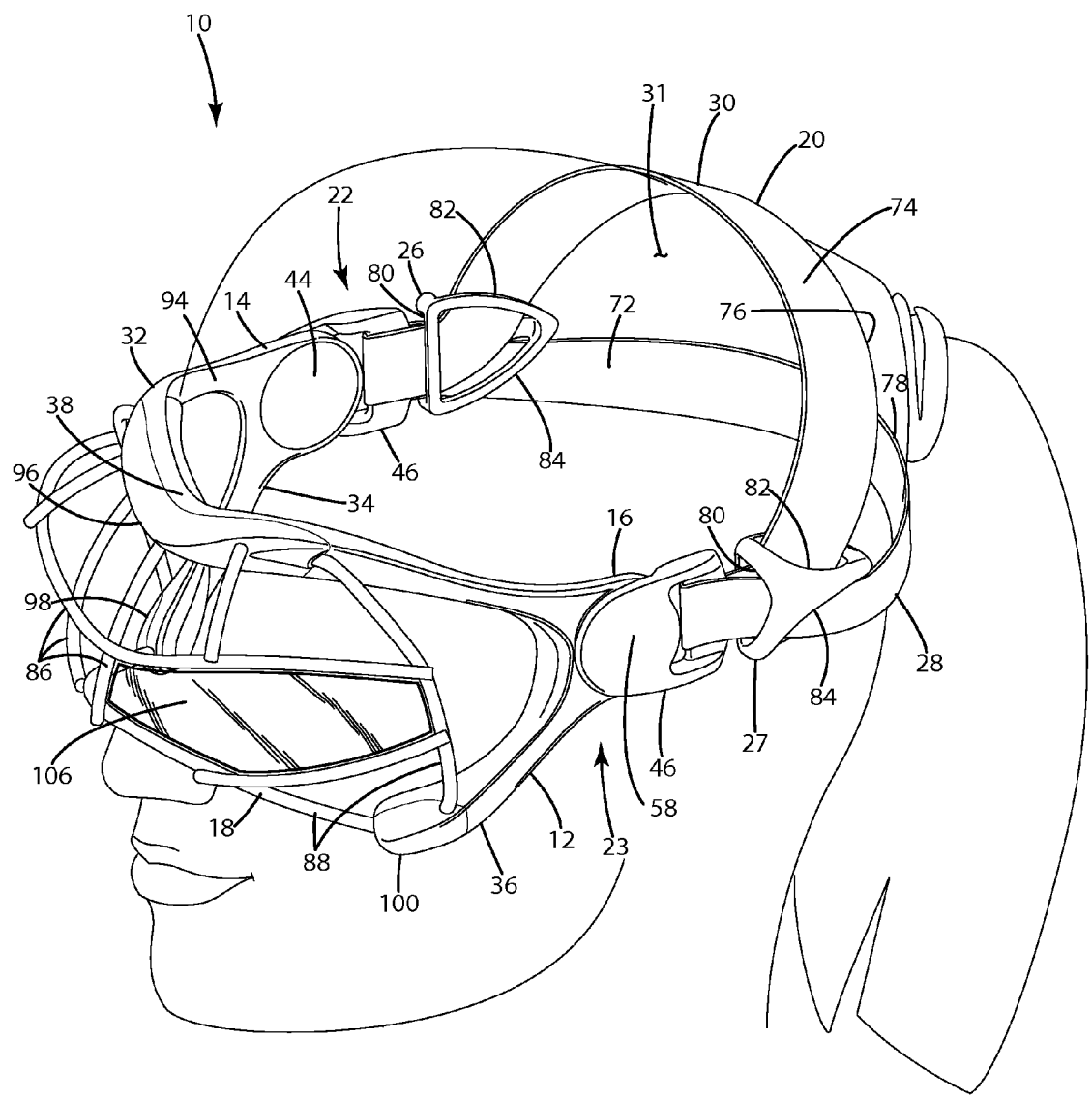
FIG. 1 is a front perspective view of a current embodiment of the protective eyewear in accordance with the present invention.

Protective eyewear in accordance with the present invention is shown in FIG. 1 and is generally designated 10. The protective eyewear 10 includes a frame 12 having a first end 14 and an opposing second end 16. An eye protector 18 is joined with the frame 12. A flexible strap 20 is joined with the first and second ends 14, 16 of the frame 12 and is adapted to extend around at least a portion of a player's head to position the eye protector 18 over the player's eyes. A connector 22 is rotatably joined with the first side 14 of the frame 12 so that the connector 22 rotates in a plane generally parallel to the player's temple. The connector 22 includes a rotation limiter 24 that limits its rotation, which will be discussed in more detail below. The connector 22 is joined with the strap 20 so that the strap 20 can rotate relative to the frame at its connection to the frame. A strap diverter 26 is adjustably positioned along the strap 20 and divides the strap 20 into first and second strap portions 28 and 30 extending at an angle relative to one another and defining a space 31 therebetween.

The frame 12 can be formed in any shape that is suitable to support and retain the eye protector 18 and to join with the strap 20. In the illustrated embodiment, the frame 12 includes a substantially horizontal upper frame portion 32, which generally corresponds to a player's forehead when the eyewear 10 is worn. The upper frame portion 32 is slightly indented or V-shaped at or near its the center 38, which rests on the player's forehead generally above the player's nose. The upper frame portion 32 angles down toward and terminates at the first and second ends 14 and 16, which generally correspond to the player's temples. The frame 12 also includes two lower frame portions 34 and 36, which extend from the ends 14 and 16 of the frame, respectively, on a downward angle toward the player's face. The lower frame portions 34 and 36 both terminate at the respective sides of the player's face and generally correspond to the player's cheeks. Thus, the frame 12 is positioned around the player's eyes so as not to obstruct the player's vision. Although not shown, the lower frame portions 34, 36, if desired, can extend over the player's nose and connect so that the lower portion of the frame is closed by those portions. The frame 12 can be formed from any suitable material, including but not limited to rubber and plastic materials, such as thermoplastic elastomers, polyurethane, neoprene, polyethylene and can be rigid or flexible or partially flexible.

Figure 3:
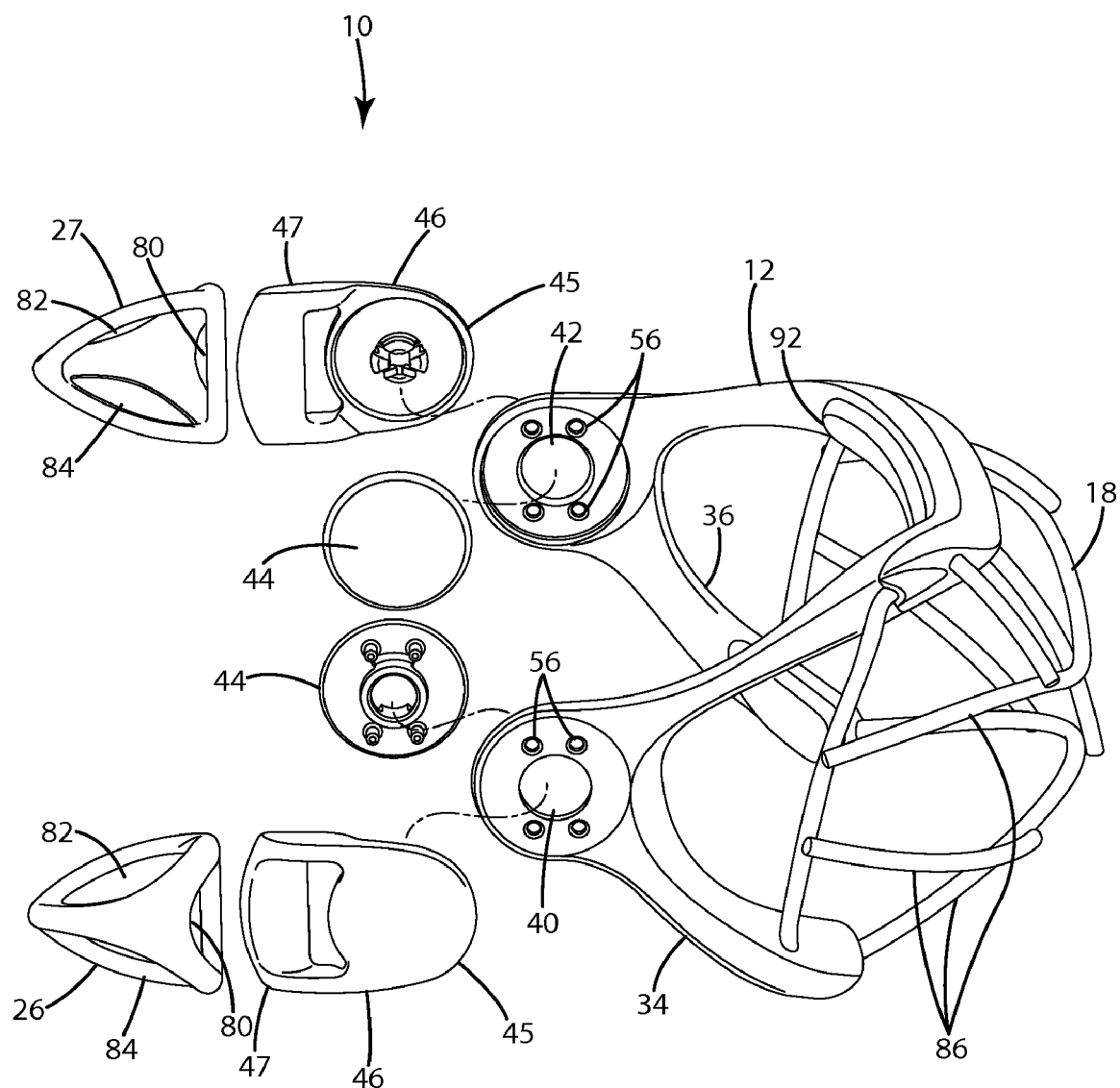
FIG. 3 is an exploded view of the protective eyewear.

The protective eyewear 10 can include an additional connector 23, which, along with connector 22, is adapted to connect the strap 20 to the frame 12. In the illustrated embodiment, the connector 22 joins a portion of the strap 20 to the first end 14 of the frame 12, and the connector 23 joins another portion of the strap 20 to the second end 16. As shown in FIG. 3, each of the first and second ends 14 and 16 of the frame 12 can define an aperture 40, 42. The aperture 40 is adapted to receive a portion of the connector 22, and the aperture 42 is adapted to receive a portion of the connector 23. The connectors 22 and 23 can be formed in any suitable size and shape to connect the strap 20 to the frame 12 or to the eye protector 18. Because the connectors 22 and 23 are identical or substantially similar in the illustrated embodiment, only the connector 22 will be described in detail.

Figure 4:
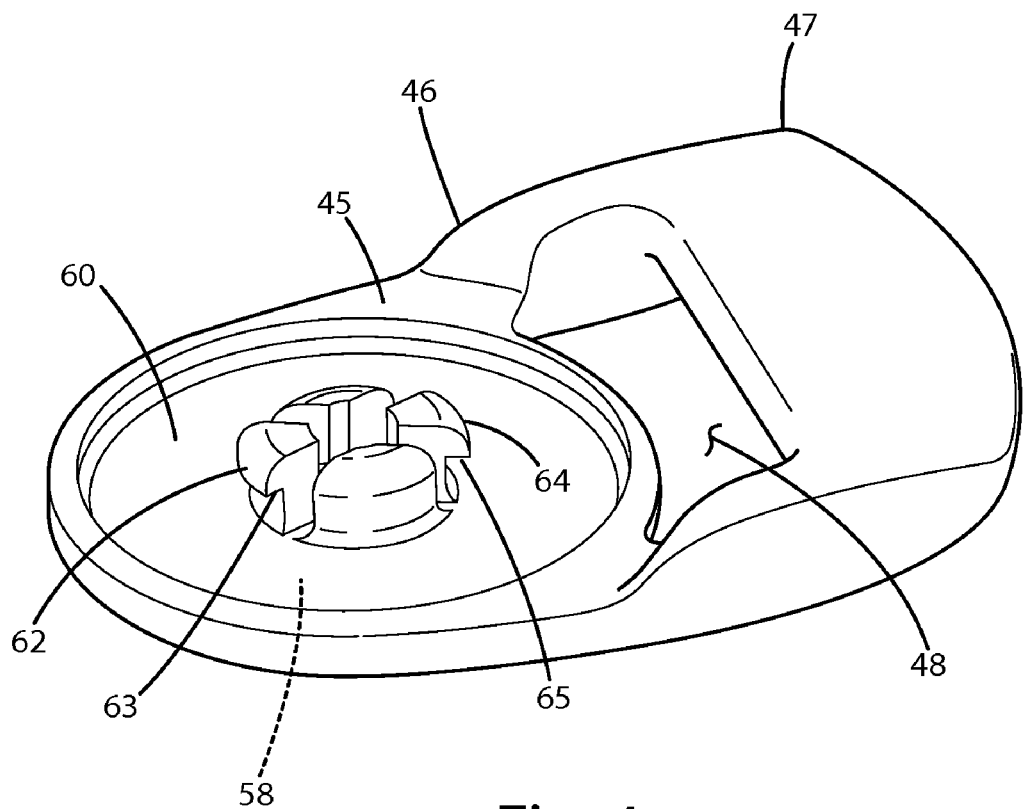
FIG. 4 is a perspective view of a swivel portion of a connector of the eyewear.
Figure 5:
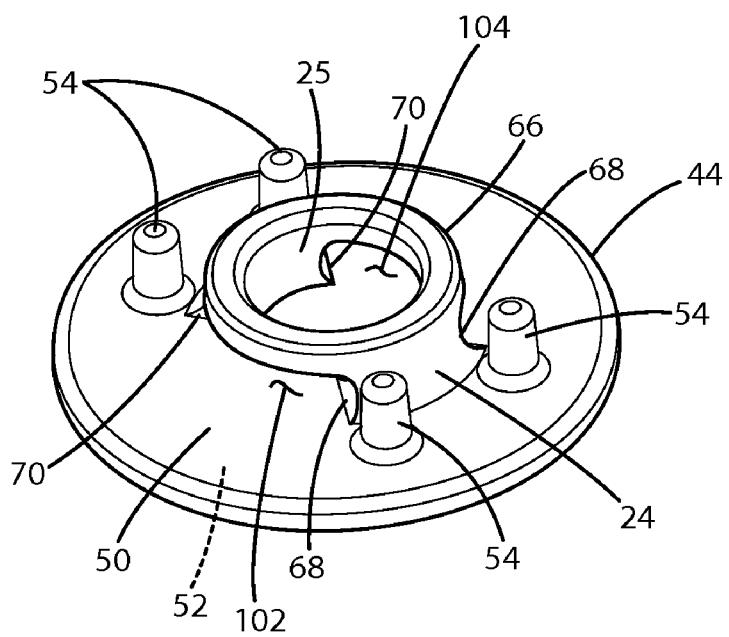
FIG. 5 is a perspective view of a base portion of the connector of the eyewear.

As shown in FIGS. 3-5, the connector 22 includes a base 44 that is adapted to be joined with a swivel portion 46. The swivel portion 46 includes a frame connection portion 45 and a strap connection portion 47 (FIG. 4). The frame connection portion 45 can be rotatably located in an aperture 40 defined in the frame 12 and is adapted to rotate the swivel portion 46 in a plane generally parallel to the temple or side of the head of the player when the protective eyewear 10 is worn. The frame connection portion 45 can also be rotatably mounted in the track 66 of base 44. The strap connection portion 47 of the swivel portion 46 defines an aperture 48 adapted to receive the strap 20 to join the strap 20 with the frame 12. Thus, the swivel portion 46 can be rotated to adjust the angle of the strap 20 with respect to the frame 12, so that the strap 20 can be positioned higher or lower on the player's head, or generally at different angles on the player's head as the strap extends rearward from the face.

The swivel portion 46 is adapted to engage the base 44 to assist in retaining the swivel portion 46 in the aperture 40 in the frame 12. In the illustrated embodiment, the swivel portion 46 includes an outer surface 58 and an inner surface 60 adapted to face an inner surface 50 of the base 44 (FIGS. 4 and 5). Two snap elements 62, 64 extend from the inner surface 60 of the swivel portion 46 and are adapted to snap around or under a track 66 formed on the inner surface of the base 44. The snap elements 62, 64 can then slide along the track 66, such that the swivel portion 46 is adapted to rotate with respect to the base 44. Optionally, the base 44 can be fixed and non-rotatable relative to the frame 12, such that the swivel portion 46 can rotate with respect to both the base 44 and the frame 12. As shown in FIGS. 3 and 5, multiple protrusions 54 extend from the inner surface 50 of the base 44. The protrusions 54 are adapted to be inserted into openings 56 defined in the first end 14 of the frame 12. When the protrusions 54 are inserted into the openings 56, the position of the base 44 is fixed with respect to the frame 12. These protrusions can be fixed within the frame by molding or with suitable fasteners; of course, the protrusions and openings can be reversed on the base and frame as desired. Optionally, the protrusions and openings are designed so that the rotation limiter 24 registers with the swivel in a manner to provide the desired rotation limits.

Figure 6:
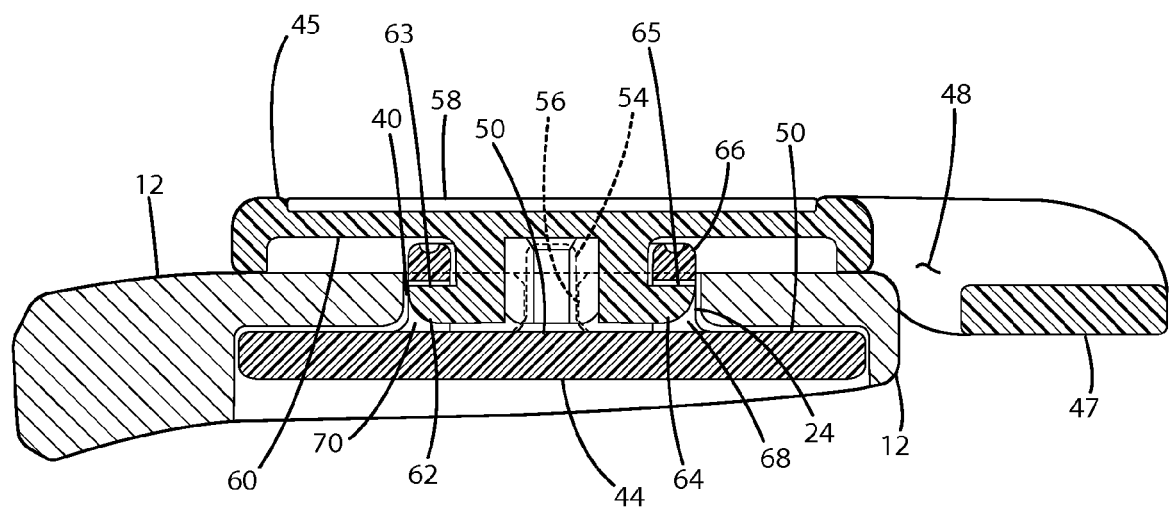
FIG. 6 is a sectional view taken along lines 6-6 in FIG. 2.

With reference to FIGS. 5 and 6, the track 66 can be selectively formed depending on the range and direction of motion desired for the swivel portion 46. The track 66 can be generally formed as a circular ring that is spaced from and parallel with the inner surface 50 of the base 44. The snap elements 62, 64 are each generally adjusted to flex a certain amount, when inserted into the hole 67, so that the lips 63 and 65 of those elements pass the track 66. After the lips pass the track, each lip portion 63 and 65 resiliently snaps under the track 66, in the respective recesses 102, 104 between the track 66 and the inner surface 50 of the base 44 (FIG. 6). The snap elements 62, 64 can then slide along the track 66 within the respective recesses 102, 104 to allow the swivel portion 46 to rotate.

Optionally, the track 66 may include at least one rotation limiter to limit the rotational movement of the swivel portion 46. Referring to FIG. 5, the track 66 is joined to the inner surface 50 of the base 44 by two rotation limiters 24 and 25, which are spaced apart at generally opposite sides of the track 66. As shown in FIG. 5, the rotation limiter 24 forms abutment portions 68, and the rotation limiter 25 forms abutment portions 70. Optionally, one of these abutment portions can be eliminated, or additional abutment portions can be added as desired. The snap elements 62, 64 can move along the track 66 until the snap elements 62, 64 engage the abutment portions 68 and 70. This engagement of the elements 62, 64 with the abutment portions 68, 70 limits the rotational movement of the swivel portion 46 (FIGS. 5 and 6). Thus, the swivel portion 46 and the strap 20 are prevented from rotating too far upward over the player's head or too far downward toward the player's neck.

The protective eyewear 10 can be retained over the player's face in any suitable manner. As illustrated in FIG. 1, the strap 20 is used to retain the protective eyewear 10 over the player's face; however, the protective eyewear 10 could alternatively include a pair of end pieces adapted to sit over the player's ears, like a traditional pair of eyeglasses. The strap 20 can be formed from an elastic material to allow the player to stretch the strap 20 so that the protective eyewear 10 can be properly positioned on the player's head. After the player adjusts the frame 12 and the eye protector 18 in the correct position, the elastic force of the strap will tighten the eyewear 10 against the player's face and head.

With reference to FIG. 1, the strap 20 is threaded through the openings 48 in the respective connectors 22 and 23, and the ends of the strap 20 are connected together to form a closed loop. In this configuration, a portion 30 of the strap 20 is located adjacent the player's head, and a portion 28 overlaps or overlays the strap portion 30, such that an inner surface 72 of the strap portion 28 contacts and rests against an outer surface 74 of the strap portion 30 when the strap is stretched over the player's head.

The protective eyewear 10 can include at least one strap diverter for directing the strap portions 28 and 30 over specific areas of the player's head. For example, two strap diverters 26 and 27 can retain the strap portions 28 and 30 together at two locations along the strap 20. As shown in FIG. 1, the diverters 26 and 27 retain the strap portion 28 over the strap portion 30 in the area between the respective diverters 26, 27 and connectors 22, 23. As the strap portion 28 exits the diverters 26 and 27, the diverters 26 and 27 direct the strap portion 28 at a downward angle from the diverters 26 and 27. As the strap portion 30 exits the diverters 26 and 27, the diverters 26 and 27 direct the strap portion 30 at an upward angle from the diverters 26 and 27. As a result, a space or opening 31 is created between a lower surface 76 of the strap portion 30 and an upper surface 78 of the strap portion 28. Optionally, the opening 31 can be sized to accommodate a player's loose hair or ponytail as shown in FIG. 1. The opening 31 also allows the elastic force of the strap 20 to be distributed more evenly across the back of the player's head.

The position of the first and second diverters 26 and 27 along the strap 20 is adjustable, such that the size and the location of the opening 31 can be adjusted. For example, the size of the opening 31 could be tightened or widened to accommodate the player's ponytail or to adjust the distribution of elastic force from the strap 20. Optionally, the opening 31 can be tightened to secure the strap 20 about a lacrosse stick or other piece of equipment for storage or transportation when the protective eyewear 10 is not being worn. The diverters 26 and 27 can be adjusted by sliding the diverters 26, 27 along the strap 20 to the desired location.

Figure 2:
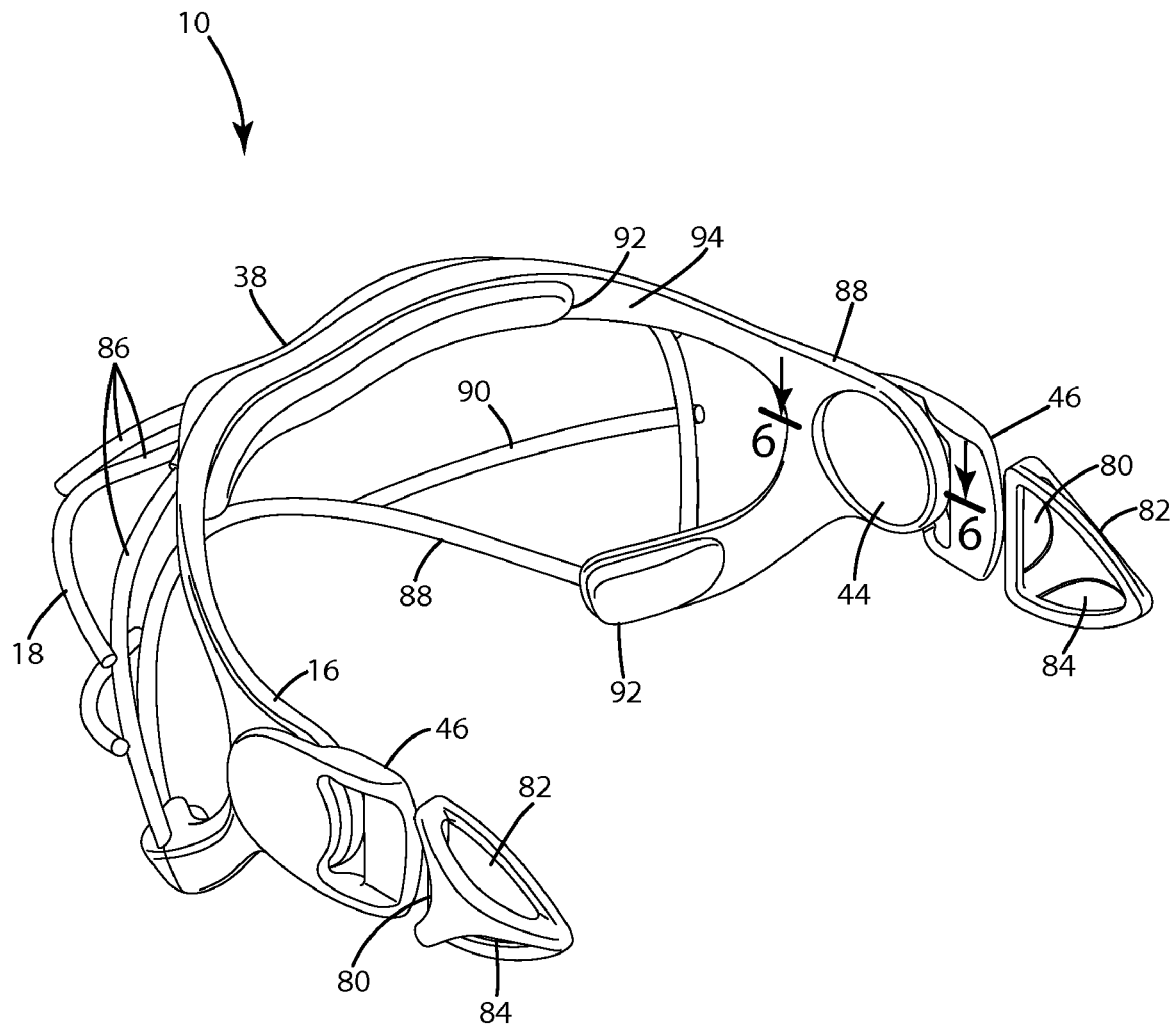
FIG. 2 is a rear perspective view of the protective eyewear.

The first and second diverters 26 and 27 can be formed in any suitable shape and size to divert and converge the strap portions 28 and 30 to create the opening 31. The diverters can be identical, such that only diverter 26 can be described in detail. As shown in FIGS. 1-2, the diverter 26 can be generally triangular in shape and defines an opening 80 at one end. The opening 80 is spaced from the connector 22 and faces the strap connection portion 47 of the swivel portion 46 of the connector 22. The opening 80 is adapted to receive the strap portions 28 and 30 in a generally horizontal, overlapped orientation. The diverter 26 includes two additional openings or exits 82 and 84, through which the strap portions 28 and 30 exit the diverter 26. The exits 82 and 84 are positioned at an angle with respect to the opening 80, such that the exits 82, 84 divert and change the direction of the strap portions 28 and 30. The exit 82 is adapted to receive and divert the strap portion 30 at an upward angle, and the exit 84 is adapted to receive and divert the strap portion 28 at a downward angle. The diverter 27 is positioned between the diverter 26 and the connector 23 and diverts the strap portions 28 and 30 in a similar manner as diverter 26, such that the opening 31 is created between the diverters 26, 27.

With reference to FIGS. 1 and 2, the eye protector 18 can be formed in any configuration suitable to help protect the player's eyes from blows during play, while maintaining the player's line of sight. The eye protector 18 can be formed as a cage, which includes a network of wire elements 86. The wire elements 86 can provide spring action that can dissipate impact and shock more effectively than other types of eye protectors, such as goggles. To maintain an unobstructed central field of view for the player, in the illustrated embodiment, the wire elements 86 are arranged so that no wire element 86 is directly in front of the player's eyes. However, the openings between the wire elements 86 are arranged to be sufficiently close together to prevent objects such as lacrosse sticks or lacrosse balls from penetrating between the wire elements 86. Optionally, at least one lens 106 can be included between the wire elements 86. Further optionally, although shown as a cage, the eye protector 18 can be formed as a lens, for example a polycarbonate lens, joined with the frame. Even further optionally, the eye protector 18 can be formed as a lens that is integral with the frame 12, without a wire cage.

The wire elements 86 can be formed from any suitable material, including metals, alloys, composite or synthetic materials. Optionally, the wire elements 86 can be formed from mild spring steel wire, which can meet the ASTM standard for women's adult and youth lacrosse. The wire elements 86 can be weldable and formable, to allow the wire elements 86 to be resistance-welded or spot-welded to each other. Optionally, the wire elements 86 can have a protective coating, such as rubber or a synthetic material, and can be finished to remove any sharp edges that could cut a player.

The configuration of the wire elements 86 and the way that the wire elements 86 are stacked can affect the strength of the protective eyewear 10. For example, in the illustrated embodiment, the outer or perimeter wire elements 88 are generally positioned below the inner wire elements 90, such that the ends of the inner wire elements 90 overlap the perimeter wire elements 88 (FIG. 2). In this configuration, upon impact, the force can be better distributed away from the face, as opposed to toward the face, and the spring effect of the wire elements 86 can maximized.

The wire elements 86 can be joined with the frame 12 in any suitable manner. For example, the frame 12 can be adapted to receive a portion of at least some of the wire elements 86. As shown in FIG. 1, the perimeter wire elements 88 are joined with the frame 12 by three wire element connectors 96, 98 and 100, positioned respectively at the upper frame portion 32 and the ends of the lower frame portions 34 and 36. The wire element connectors 96, 98 and 100 are positioned over a portion of the wire elements 86 and are molded to, joined with and/or adhered to the frame 12 on opposite sides of the wire elements 86 to retain the wire elements 86 to the frame 12.

The protective eyewear 10 can be formed to cover any desired portions of the face. For example, in addition to covering the player's eyes, the protective eyewear 10 of the illustrated embodiment covers the player's facial area around the eyes and a portion of the player's temples and nose.

As shown in FIG. 2, the protective eyewear 10 can include padded portions 92 on an inner surface 94 of the frame 12. The padded portions 92 can be adapted to provide a comfortable barrier between the player's face and the frame 12, such that the player's face substantially engages the padded portions 92 and not the remaining portion of the frame 12. The padded portions 92 can be selectively positioned on the inner surface 94 of the frame 12 to engage desired portions of the player's facial area. For example, the padded portions 92 are positioned on the upper frame portion 32 and on the ends of the lower frame portions 34 and 36. Optionally, the padded portions 92 can be removable from the frame 12, such that the player can selectively attach and remove the padded portions 92 from the frame 12 as desired.

The padded portions 92 can be formed from any suitable material, such as a material that will not cause skin irritation or undergo substantial physical changes as a result of contact with the face or skin. For example, the padded portions 92 can be formed from a low density foam material or a polymeric material. Optionally, the padded portions 92 can include a dual-density open or closed cell foam, for example, using a three pound density foam in contact with the face and a six pound density foam layer against the frame 12. The lower density layer can be more comfortable against the face, while the higher density foam can provide better impact protection.

As desired, the protective eyewear 10 can be customized to reflect the player's team name, logo, colors or other identifier. For example, the outer surface 58 of the swivel portion 46 and/or the outer surface 52 of the base 44 can be adapted to include the identifier, which can be molded or printed thereon. Additionally, the various elements of the protective eyewear 10 can be molded or formed from materials in the player's team colors.

While the illustrated embodiment has been described in connection with the sport of women's lacrosse, it should be understood that the protective eyewear of the present invention is suitable for use by both male and female players of an essentially unlimited number of indoor and outdoor sports and other non-sport activities.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The embodiments of the invention in which an exclusive property or privilege is claimed are defined as follows:

1. A protective eyewear comprising:
   a frame having a first side and an opposing second side;
   an eye protector joined with the frame;
   a flexible strap joined with the first and second sides of the frame, the strap adapted to extend around at least a portion of a player's head to position the eye protector over the player's eyes; and
   a connector rotatably joined with the first side of the frame so that the connector rotates in a plane generally parallel to a temple of the player, the connector joined with the strap so that the strap is rotatable relative to the frame; and
   a strap diverter positioned along the strap, the strap diverter dividing the strap into first and second strap portions extending at an angle relative to one another and defining a space therebetween, wherein the diverter is adjustably positionable along the strap,
   wherein the connector includes a base and a swivel portion joined together, the swivel portion being at least partially rotatably mounted in an aperture defined in the frame.

2. The protective eyewear of claim 1 wherein the base is non-rotatable relative to the frame.

3. The protective eyewear of claim 2 wherein the connector includes a rotation limiter having an abutment portion joined with the base and adapted to engage the swivel portion to limit the rotational movement of the swivel portion.

4. A protective eyewear comprising:
   a frame having a first side and an opposing second side;
   an eye protector joined with the frame;
   a flexible strap joined with the first and second sides of the frame, the strap adapted to extend around at least a portion of a player's head to position the eye protector over the player's eyes; and
   a connector rotatably joined with the first side of the frame so that the connector rotates in a plane generally parallel to a temple of the player, the connector joined with the strap so that the strap is rotatable relative to the frame; and
   a strap diverter positioned along the strap, the strap diverter dividing the strap into first and second strap portions extending at an angle relative to one another and defining a space therebetween, wherein the diverter is adjustably positionable along the strap,
   wherein the connector includes a rotation limiter that limits the rotation of the connector within a pre-selected angle.

5. The protective eyewear of claim 4 wherein the eye protector is a cage formed from a plurality of wire elements configured to allow the player to participate in an activity, yet protect the player's eyes from blows thereto.

6. A protective eyewear comprising:
   a frame, including at least one flexible portion, and opposing sides;
   a cage joined with the frame for protecting the eyes of a player, the cage being formed from a plurality of wire elements configured to allow the player to participate in an activity, yet protect the player's eyes from blows thereto;
   a flexible strap joined with the opposing sides of the frame, the strap adapted to extend around at least a portion of the player's head to retain the eyewear in a position over the player's eyes; and
   first and second connectors that join the strap to the opposing sides of the frame, the connectors each including a base and a swivel portion joined together, the swivel portion being rotatably mounted in an aperture defined in the frame; and
   wherein the base is non-rotatable relative to the frame, the base including at least one abutment portion adapted to engage the swivel portion to limit the rotational movement of the swivel portion.

7. The protective eyewear of claim 6 wherein the base includes a track, wherein at least a portion of the swivel portion is adapted to travel around the track.

8. The protective eyewear of claim 7 wherein at least a portion of the track is spaced from an inner surface of the base, wherein the swivel portion includes at least one snap element adapted to snap into a space between the track and the inner surface of the base.

9. The protective eyewear of claim 8 wherein the at least one abutment portion is adapted to engage the at least one snap element to limit the rotational movement of the swivel portion within a predetermined angle.

10. The protective eyewear of claim 6 wherein the swivel portion is rotatable in a plane that is generally parallel to the temple of a user.

11. The protective eyewear of claim 6 wherein the base includes at least one protrusion, wherein the frame defines at least one opening adapted to receive the protrusion, wherein the at least one protrusion prevents rotational movement of the base with respect to the frame when the at least one protrusion is received in the at least one opening.

12. The protective eyewear of claim 6 wherein the cage is lenseless.

13. The protective eyewear of claim 6 wherein the cage includes at least one lens.

14. A protective eyewear comprising:
   a frame including opposing ends;
   a cage joined with the frame for protecting the eyes of a player, the cage being formed from elongated wire elements joined together;
   a flexible strap joined with the frame that extends about the player's head to retain the eyewear in a position over the player's eyes;
   at least two connectors adapted to join the strap at each of the opposite ends of the frame, wherein the connectors and the strap are adapted to rotate with respect to the frame, wherein at least one of the connectors includes a rotation limiter that limits the rotational movement of the connector;
   wherein the strap extends from each of the connectors, wherein the ends of the strap are joined with first and second strap portions;

a first diverter positioned along the strap, the first diverter diverting the first and second strap portions in different directions, wherein a space is created between the first and second strap portions;

a second diverter positioned along the strap, the second diverter converging the first and second strap portions, wherein the first and second strap portions are overlapped as they exit the second diverter;

wherein the positions of the first and second diverters along the strap are adjustable.

15. The protective eyewear of claim 14 wherein the space is created between a lower edge of the first strap portion and an upper edge of the second strap portion.

16. The protective eyewear of claim 15 wherein a rear surface of the first strap portion is adjacent the front surface of the second strap portion when the first and second strap portions are overlapped.

17. The protective eyewear of claim 16 wherein the first and second diverters each include an opening and at least two exits, the at least two exits being adapted to direct the first and second strap portions in the different directions.

18. The protective eyewear of claim 17 wherein the openings of the first and second diverters are each adapted to face one of the connectors, wherein the first and second strap portions are overlapped between the opening in the first diverter and one of the connectors and between the second diverter and the other of the connectors.

19. The protective eyewear of claim 18 wherein the connector includes a base that is non-rotatable relative to the frame and a swivel portion joined with the base, the swivel portion being at least partially rotatably mounted in an aperture defined in the frame.

20. The protective eyewear of claim 19 wherein the rotation limiter is formed as at least one abutment portion positioned on the base and adapted to engage the swivel portion to limit the rotational movement of the swivel portion.

* * * * *